United States Patent [19]

Ishiwatari et al.

[11] Patent Number: 4,857,304

[45] Date of Patent: Aug. 15, 1989

[54] COSMETIC COMPOSITION

[75] Inventors: Masaaki Ishiwatari; Yuji Tsutsumi; Yoshiyuki Ogusu; Yoshihiro Kimura, all of Yokohama, Japan

[73] Assignee: Shiseido Company Ltd., Tokyo, Japan

[21] Appl. No.: 7,303

[22] Filed: Jan. 27, 1987

[30] Foreign Application Priority Data

Jan. 28, 1986 [JP] Japan .................................. 61-16084

[51] Int. Cl.$^4$ ........................ A61K 7/02; A61K 7/031; A61K 7/32; A61K 7/42; A61K 7/44; A61K 7/48
[52] U.S. Cl. ........................................ 424/59; 424/60; 424/63; 424/83; 514/844; 514/845; 514/848
[58] Field of Search ........................ 424/59, 60, 63, 83

[56] References Cited

U.S. PATENT DOCUMENTS

| | | | |
|---|---|---|---|
| 3,932,614 | 1/1976 | Scott | 424/83 |
| 4,426,374 | 1/1984 | Wheeler | 424/60 |

OTHER PUBLICATIONS

Brevet Special De Medicament, 12/15/69, Seilinger.

*Primary Examiner*—Dale R. Ore
*Attorney, Agent, or Firm*—Sprung Horn Kramer & Woods

[57] ABSTRACT

A cosmetic composition comprising at least one fluorocarbon having the formula $C_nH_pF_qX_4$ wherein X represents chlorine or bromine, n is an integer of 1 to 8, q is an integer of 1 to 18, and p+q+r is an 2n+2, which is liquid at an ambient temperature and has a boiling point of 200° C. or less, in the composition. This cosmetic composition does not exhibit an unpreferable oily feeling finish but does exhibit a cosmetic finish which lasts for a long time.

4 Claims, No Drawings

COSMETIC COMPOSITION

BACKGROUND OF THE INVENTION

1. Field of the Invention

The present invention relates to a cosmetic composition containing a fluorocarbon, which is liquid at an ambient temperature. More specifically, it relates to a makeup type cosmetic composition containing a fluorocarbon, which is liquid at an ambient temperature and has a boiling point of 200° C. or less.

2. Description of the Related Art

When formulating ingredients for cosmetics, in particular, makeup cosmetic, the compositions thereof must exhibit proper safety and sufficient cosmetic effects. However, since conventional oily makeup cosmetic compositions contain as a main ingredient mineral oils or ester oils, the cosmetic compositions are disadvantageous in that an oily feeling is exhibited during or after the application, and in that the cosmetic finish after the application does not last for a long time.

To alleviate the above-mentioned disadvantages, a volatile oil has been recently used in the art. The cosmetic compositions containing volatile oils formulated therein have advantages in that the inherent sticky or viscous feeling of oil exhibited during or after the application are not shown, and that, since the oil component is volatilized from the skin, and therefore, does not remain on the skin, the affect on the cosmetic finish by, for example, sweat, tears, or sebum, is reduced. For this reason, hydrocarbons having a relatively low boiling point or cyclic or linear dimethylpolysiloxanes having a relatively low polymerization degree have been used as the volatile oil component.

However, since hydrocarbons having a low boiling point are likely to attack polymeric substances such as plastics, the quality of the cosmetic compositions contained in cosmetic vessels made of plastics is often denatured, prior to the use thereof by consumers. On the other hand, since the volatilization rate of cyclic or linear polysiloxanes having a relatively low polymerization degree is relatively slow, certain ingredients such as pigments enter into the grooves of the skin, and thus adverse affects on the desired cosmetic finish are caused by the movements of the skin (e.g., an eyelid) immediately after the application of the cosmetic compositions, or the cosmetic compositions after the application are transferred to other portions of the skin or to clothes or accessories.

SUMMARY OF THE INVENTION

Accordingly, the objects of the present invention are to eliminate the above-mentioned disadvantages of the prior art and to provide a cosmetic composition that does not exhibit an unpreferable oily feeling finish but does exhibit a cosmetic finish which lasts for a long time.

Other objects and advantages of the present invention will be apparent from the following description.

In accordance with the present invention, there is provided a cosmetic composition comprising at least one fluorocarbon having the formula $C_nH_pF_qX_r$ wherein X represents chlorine or bromine, n is an integer of 1 to 8, q is an integer of 1 to 18, and $p+q+r$ is $2n+2$, which is liquid at an ambient temperature and has a boiling point of 200° C. or less, preferably 180° C. or less, in the composition.

DESCRIPTION OF THE PREFERRED EMBODIMENT

According to the present invention, the above specified fluorocarbon is formulated into various kinds of conventional cosmetic compositions, especially cosmetic makeup compositions (e.g., foundation, eye shadow, suntan oil, lotion, eye liner, liquid mascara, liquid eye brow).

Examples of the fluorocarbons usable in the present invention are trichloromonofluoromethane, tetrachlorodifluoroethane, trichlorotrifluoroethane, dibromotetrafluoroethane, trichlorodifluoroethane, tetrachlorotrifluoropropane, dichlorodifluorobutane, dibromomonofluorolbutane, trichlosodifluoropentane.

Although there are no specific limitations to the amount of the fluorocarbon formulated into the present cosmetic composition, the fluorocarbon is preferably formulated in an amount of 0.5% to 80% by weight, more preferably 1% to 70% by weight, based on the total amount of the composition.

The fluorocarbons usable in the present invention have a high skin safety and the volatilization rate is extremely high, the use of the fluorocarbons in, for example, makeup cosmetic compositions, is quite suitable. In addition, when the fluorocarbons are formulated into cosmetic composition base, the extendability of the resultant cosmetic composition becomes very good and a desirable refreshing feeling can be advantageously obtained. Furthermore, since the fluorocarbon does not affect polymer compounds such as rubber and plastics and metals, the quality of the resultant cosmetic composition is not denatured even during storage for a long time.

Since the fluorocarbons are freely dissolved in hydrocarbons having a low boiling point and cyclic or linear dimethylpolysiloxanes having a low polymerization degree, the volatilization rate of the fluorocarbons can be optionally adjusted by mixing with the hydrocarbons or the dimethylpolysiloxanes.

The cosmetic compositions according to the present invention may contain, in addition to the fluorocarbon, any conventional cosmetic ingredients used in cosmetic compositions.

Examples of such conventional ingredients are water, oils, waxes, alcohols, surfactants, thickening agents, humectants, pigments, dyes, perfumes, active agents such as sunscreen agents, vitamins, hormones amino acids, antioxidants, etc.

EXAMPLE

The present invention will be further explained by, but is by no means limited to, the following Example, wherein "%" in the formulation amounts of the Examples are by weight unless otherwise specified.

EXAMPLE 1: PREPARATION OF EYE SHADOW (Formulation)

| Ingredient | % |
| --- | --- |
| (1) Trichlorotrifluoroethane | 36 |
| (2) Solid paraffin | 10 |
| (3) Liquid paraffin | 10 |
| (4) Sorbitan sesquioleate | 1 |
| (5) Organically modified montmorillonite | 3 |
| (6) Ultramarine blue | 6 |
| (7) Titanium coated mica | 20 |
| (8) Mica | 10 |

-continued

| Ingredient | % |
| --- | --- |
| (9) Talc | 4 |
| (10) Perfume | q.s. |

(Preparation)

The ingredients (1) to (5) were dissolved or dispersed upon heating and the ingredients (6) to (10) were added thereto, and the mixture agitated in a homodisper. The mixture was then cooled to room temperature. Thus, the desired eye shadow was obtained.

During an actual application test of the resultant eye shadow, it was found that the product exhibited a good extendability and stumpability and an excellent cosmetic finish durability.

EXAMPLE 2: PREPARATION OF WATER-PROOF FOUNDATION (Formulation)

| Ingredient | % |
| --- | --- |
| (1) Trichlorotrifluoroethane | 20 |
| (2) Trichlorodifluoroethane | 5 |
| (3) Decamethylcyclopentasiloxane | 34 |
| (4) Organosilicon resin | 10 |
| (5) Dimethylpolysiloxane (viscosity = 6 c.s.) | 5 |
| (6) Sorbitan sesquioleate | 1 |
| (7) Pigment* | 25 |
| (8) Perfume | q.s. |

| *Composition of Pigment | % |
| --- | --- |
| Titanium dioxide | 40 |
| Talc | 25 |
| Mica | 25 |
| Iron oxide (yellow) | 2.7 |
| Iron oxide (red) | 6.5 |
| Iron oxide (black) | 0.8 |

(Preparation)

The ingredients (1) to (8) were agitated in a homodisper to obtain the desired water-proof foundation. During an actual application test of the resultant foundation, it was found that the product exhibited a refreshing feeling and a good cosmetic finish durability, and was especially suitable for use in the summer.

EXAMPLE 3: PREPARATION OF SUNTAN OIL (Formulation)

| Ingredient | % |
| --- | --- |
| (1) Tetrachlorodifluoroethane | 50 |
| (2) Trichlorodifluoroethane | 19 |
| (3) Methylphenylpolysiloxane (viscosity = 15 c.s./25° C.) | 30 |
| (4) Isooctyl p-Dimethylaminobenzoate | 1 |
| (5) Perfume | q.s. |

(Preparation)

The ingredient (4) was dissolved in the ingredient (3) and the ingredients (1) and (2) were added thereto. The mixture was then agitated to obtain the desired suntan oil. During an actual application test of the resultant suntan oil, it was found that the product had refreshing and cooling effects.

EXAMPLE 4: PREPARATION OF SUMMER LOTION (?)

(Formulation)

| Ingredient | % |
| --- | --- |
| (1) Dibromotetrafluoroethane | 0.5 |
| (2) Trichlorotrifluoroethane | 1 |
| (3) Liquid paraffin | 3 |
| (4) Olive oil | 5 |
| (5) POE* (20)-2-octyldodecanol | 2 |
| (6) Water | 83.5 |
| (7) 1,3-Butyleneglycol | 5 |
| (8) Perfume | q.s. |

(Preparation)

The ingredients (1) to (7) were emulsified to obtain the desired summer lotion. During an actual application test of the resultant summer lotion, it was found that the product had refreshing and cooling effects.

We claim:

1. An improved cosmetic make-up composition selected from the group consisting of foundation, eyeshadow, eyeliner, liquid mascara, lotion, suntan oil and liquid eye brow wherein the improvement comprises at least one fluorocarbon having the formula $C_nH_pF_qX_r$, wherein X represents chlorine or bromine, N is an interger of 1 to 8, q is an integer of 1 to 18, and $p+q+r$ is $2n+2$, which is liquid at an ambient temperature and has a boiling point of 200° C. or less, which extends and improves the cosmetic finish of the composition.

2. A cosmetic makeup composition as claimed in claim 1, wherein said fluorocarbon is at least one member selected from the group consisting of trichloromonofluoromethane, tetrachlorodifluoroethane, trichlorotrifluoroethane, dibromotetrafluoroethane, trichlorodifluoroethane, tetrachlorotrifluoropropane, dichlorodifluorolbutane, dibromomonofluorobutane, and trichlorodifluoropentane.

3. A cosmetic makeup composition as claimed in claim 1, wherein the amount of the fluorocarbon is 0.5% to 70% by weight based on the total weight of the composition.

4. An improved method for extending and improving the cosmetic finish of a cosmetic make-up composition selected from the group consisting of foundation, eyeshadow, eyeliner, liquid mascara, lotion, suntan oil and liquid eyebrow wherein the improvement comprises incorporating into said composition at least one fluorocarbon having the formula $C_nH_pF_qX_r$, wherein X represents chlorine or bromine, N is an integer of 1 to 8, q is an interger of 1 to 18, and $p+q+r$ is $2n+2$, which is liquid at an ambient temperature and has a boiling point of 200° C. or less.

* * * * *